United States Patent [19]
Jackson

[11] Patent Number: 5,340,453
[45] Date of Patent: Aug. 23, 1994

[54] ANALYSIS OF CARBOHYDRATES

[75] Inventor: Peter Jackson, Cambridge, Great Britain

[73] Assignee: Astroscan, Ltd., Braddan, Great Britain

[21] Appl. No.: 844,573

[22] PCT Filed: Sep. 20, 1990

[86] PCT No.: PCT/GB90/01448

§ 371 Date: Mar. 27, 1992

§ 102(e) Date: Mar. 27, 1992

[87] PCT Pub. No.: WO91/05256

PCT Pub. Date: Apr. 18, 1991

[30] Foreign Application Priority Data

Sep. 27, 1989 [GB] United Kingdom ............. 8921817.6
Jun. 26, 1990 [GB] United Kingdom ............. 9014158.1

[51] Int. Cl.$^5$ ............................................. C25B 7/00
[52] U.S. Cl. ............................ 204/182.8; 204/299 R
[58] Field of Search ..................... 204/182.8, 299 R

[56] References Cited

U.S. PATENT DOCUMENTS

| | | | |
|---|---|---|---|
| 4,975,165 | 12/1990 | Brandley et al. | 204/182.1 |
| 5,019,231 | 5/1991 | Brandley | 204/182.1 |
| 5,035,786 | 7/1991 | Brandley et al. | 204/182.1 |
| 5,104,508 | 4/1992 | Williams et al. | |

FOREIGN PATENT DOCUMENTS

| | | |
|---|---|---|
| 8810422 | 12/1988 | World Int. Prop. O. |
| WO91/05265 | 4/1991 | World Int. Prop. O. |
| WO91/12275 | 8/1991 | World Int. Prop. O. |
| WO91/12520 | 8/1991 | World Int. Prop. O. |
| WO92/02816 | 2/1992 | World Int. Prop. O. |
| WO92/11531 | 7/1992 | World Int. Prop. O. |

OTHER PUBLICATIONS

Laemmli, U. K., "Cleavage of Structural Proteins during the Assembly of the Head of Bacteriophage T4", *Nature*, 227:680–685, Aug. (1970).

Jackson, Urwin & Mackay, "Rapid imaging, using a cooled charge-coupled-device, of fluorescent two-dimensional polacrylamide gels produced by labelling proteins in the first-dimensional isoelectric focusing gel with the fluorophore 2-methoxy-2,4-diphenyl-3(2H-)furanone", *Electrophoresis*, 9:330–339, Jul. (1988).

Rice, Rottink and Linhardt, "Fractionation of heparin-derived oligosaccharides by gradient polyacrylamide-gel electrophosphoresis", *Biochem J.*, 244:515–522, Jun. (1987).

Turnbull, J. E. & Gallagher, J. T., "Oligosaccharide mapping of heparan sulphate by polyacrylamide-gradient-gel electrophoresis and electrotransfer to nylon membrane", *Biochem. J.*, 251:597–608, Apr. (1988).

(List continued on next page.)

*Primary Examiner*—John Niebling
*Assistant Examiner*—C. Delacroix-Muirheid
*Attorney, Agent, or Firm*—Limbach & Limbach

[57] ABSTRACT

Carbohydrate substances are separated or distinguished by a method which involves labelling carbohydrate substances with a labelling reagent comprising a fluorescent naphthalene ring structure having as a substituent a reactive group capable of reacting with a reducing sugar to bind thereto and also having at least one substituent group capable of carrying a charge but which does not react with reducing sugars and does not extinguish fluorescence of the labelling reagent; applying the labelled substances to an electrophoretic gel; and running the gel to cause differential migration of different substances. The preferred labelling reagents are aminoaphthalenesulphonic acids with one, two or three sulphonic acid groups, particularly 8-aminoaphthalene-1,3,6,-trisulphonic acid (ANTS), and 1-amino-4-naphthalene sulphonic acid (ANSA).

14 Claims, 10 Drawing Sheets

OTHER PUBLICATIONS

Al-Hakim and Linhardt, "Isolation and recovery of acidic oligosaccharides from polyacrylamide gels by semi-dry electrotransfer", *Electrophoresis,* 11:23–28, Jan. (1990).

Weitzman, Scott & Keegstra, "Analysis of Glycopeptides as Borate Complexes by Polyacrylamide Gel Electrophoresis", *Anal. Biochem.,* 97:438–449, Sep. (1979).

Hardy & Townsend, "Separation of positional isomers of oligosaccharides and glycopeptides by high-performance anion-exchange chromatography with pulsed amperometric detection", *Proc. Natl. Acad. Sci. USA,* 85:3278–3293, May (1988).

Neville, D. M. Jr., "Molecular Weight Determination of Protein-Dodecyl Sulfate Complexes by Gel Electrophoresis in a Discontinuous Buffer System", *J. Biol. Chem.,* 246:6328–6334, Oct. (1971).

Jackson, D., "The use of polyacrylamide-gel electrophoresis for the high-resolution separation of reducing saccharides labelled with the fluorophore 8-aminonaphthalene-1,3,6-trisulphonic acid", *Biochem. J.,* 270:705–713, Apr. (1990).

```
Neu5Acα2-6 Galβ1-4 GlcNAcβ1
                            |
                            |
                            6
                              Galβ1-4Glc
                            3
                            |
                            |
Fucα1-2Galβ1-3GlcNAcβ1
```

Fig. 14

ANALYSIS OF CARBOHYDRATES

FIELD OF INVENTION

This invention concerns analysis of carbohydrates.

BACKGROUND TO THE INVENTION

International Publication No. WO88/10422 discloses, inter alia, techniques for analysing carbohydrate structures or distinguishing or separating carbohydrate substances, involving applying carbohydrate substances to an electrophoretic gel and running the gel to cause differential migration of different substances. The carbohydrate substances may be pre-labelled with a fluorescent labelling reagent, e.g. amino fluorescein, to impart a charge to the substance, thereby to enable electrophoretic separation, and to enable visualisation of the substances after running of the gel. In this case, visualisation may be effected with the naked eye, but enhanced sensitivity is obtained by viewing with a charge coupled device (CCD).

The present invention concerns a development of such techniques, and is based on the discovery that unexpectedly good results can be obtained by using naphthalene derivatives as the fluorescent labelling reagent.

SUMMARY OF THE INVENTION

According to the present invention there is provided a method of separating or distinguishing carbohydrate substances, comprising labelling carbohydrate substances with a labelling reagent comprising a fluorescent naphthalene ring structure having as a substituent a reactive group capable of reacting with a reducing sugar to bind thereto and also having at least one substituent group capable of carrying a charge but Which does not react with reducing sugars and does not extinguish fluorescence of the label ling reagents applying the labelled substances to an electrophoretic gel; and running the gel to cause differential migration of different substances.

The structure of naphthalene is shown in FIG. 1, with carbon atoms where groups may be substituted identified by number (1 to 8) and type (alpha and beta).

The currently preferred reactive group capable of reacting with a reducing sugar is a primary amino group ($-NH_2$), but other groups such as a hydrazino group ($-NH-NH_2$) or a secondary amino group ($-NHR$) may alternatively be used. Further possible groups will be apparent to those skilled in the art. The reactive group my be attached to any of carbons 1 to 8 of the naphthalene. The reactive group may be directly attached to the carbon, or may be indirectly attached via a linker or spacer group such as an aliphatic group. The presently preferred arrangement comprises a primary amino group directly attached to an alpha carbon of the naphthalene ring structure. It is desirable to include only one such reactive group so that only one sugar molecule will bind to each molecule of labelling reagent.

The substituent group capable of carrying a charge preferably comprises a sulphonic acid group ($-SO_3H$), which may be initially present in the form of the acid or a salt such as the sodium salt, and which ionises in solution under appropriate conditions to the form $-SO_3^-$. A wide range of other substituent groups my also be used, including for example, hydroxyl groups ($-OH$), carboxyl groups ($-COOH$), tertiary amine groups ($-NR_1R_2$) and quaternary ammonium groups ($-N^+R_1R_2R_3X^-$). Other possible groups will be apparent to those skilled in the art. Such groups may initially be in the form of salts. Such a group may be attached to one or more (e.g. two or three) available carbons of the naphthalene ring, either directly or indirectly via a linker or spacer group such as an aliphatic group.

The sulphonic acid group is the correctly preferred substituent group capable of carrying a charge. This is because the resulting compounds are stable and are negatively charged over a wide pH range which includes convenient conditions under which to carry out electrophoretic separation.

The preferred labelling reagents are thus aminonaphthalenesulphonic acids, with one, two or three sulphonic acid groups.

One presently preferred labelling reagent is 8-aminonaphthalene-1,3,6-trisulphonic acid (referred to as ANTS for brevity). The structure of ANTS is shown in FIG. 2. ANTS is commercially available, e.g. from Molecular Probes, Eugene, Oreg., U.S.A, which supplies the material in the form of the disodium salt. ANTS is particularly well suited to detection with a CCD, as is discussed below.

Other preferred labelling reagents include 1-amino-4-naphthalene sulphonic acid (referred to as ANSA), the structure of which is shown in FIG. 3. ANSA may be modified by addition of a further sulphonic acid group an available location, to produce a disulphonic acid, referred to as ANDA.

As compared with ANTS, ANSA and ANDA have less charge and generally have slower electrophoretic mobility. The most appropriate reagent can be selected for a particular situation, depending on factors such as the carbohydrate substances to be labelled, electrophoretic system used etc.

The labelling reagent may optionally carry one or more non-reactive substituent groups which do not react with reducing sugars and do not extinguish fluorescence. Such a group or groups may have the effect of modifying various characteristics of the labelling reagent, including the following: fluorescence properties, charge, reactive properties of other substitutent groups such as the reactive group, physical properties such as solubility etc. Possible non-reactive substituents include halogens, aliphatic groups, nitro groups, keto groups, aromatic groups, acetyl groups, methoxy groups etc. Other suitable groups will be apparent to those skilled in the art. Such a substituent. or substituents may be attached to any available carbon of the naphthalene, directly or indirectly.

Electrophoretic separation may be carried out in generally conventional manner, using techniques known to those skilled in the art.

The electrophoretic gel preferably comprises a relatively dense polyacrylamide gel, having a concentration in the range 15% to 60%, preferably 20% to 40%, although in some cases it may be possible or preferable to use gels of lower concentration.

The gel may be either of uniform concentration, or in the form of a gradient gel.

The gel is preferably cross linked, e.g. with N,N'methylenebisacrylamide (bis).

One presently preferred gel comprises a linear polycarylamide gradient gel having a polyacrylamide concentration (w/v) varying in a continuous gradient from 20% (top) to 40% (bottom). The gel is crosslinked with bis, at a concentration (w/v) varying from 0.53% at the lowest concentration of polyacrylamide to 1.06% at the highest concentration of polyacrylamide. Alternatively, the electrophoretic system described in Neville (reference 8) has been found to give good results.

For good resolution and sensitivity the gel is preferably run using a stacking buffer system (also known as moving boundary electrophoresis, multiphasic zone electrophoresis and other names), using techniques known for working with protein and DNA fragments, e.g. as described in the book "Gel electrophoresis of proteins: a practical approach" edited by B. D. Hames and D. Rickwood, published by IRL Press.

After running the gel the labelled carbohydrate substances, when illuminated with light of suitable wavelength, e.g. ultra violet, may be visible with the naked eye in some cases, although better resolution and sensitivity may be obtained by imaging with a CCD. Use of a CCD also has the advantage of giving readily quantitated results very quickly. Good quantitative results are easily available with a CCD due to its wide linear dynamic range. Further, a CCD can be used to view the gel while it is being run. CCDs have greatest sensitivity and quantum efficiency for light at the far red end of the spectrum, and the preferred ANTS labelling reagent is particularly well suited to detection with a CCD as it fluoresces yellow when exposed to suitable stimulating light. Furthermore, suitable stimulating light sources, such as tungsten sources, are readily and cheaply available. ANSA and ANDA fluoresce blue when suitably stimulated, and can also be detected with a CCD, possibly using a suitable filter system to improve sensitivity.

It is preferred to use a cooled 2-D CCD, operating in slow scan readout. One example of a suitable CCD system is the CCD 2200 Imaging System produced by Astromed Limited, Cambridge, United Kingdom. The CCD is preferably cooled to at least as low as $-25°$ C., with sensitivity being significantly increased by further cooling down as far as $-160°$ C. Typical operation temperatures are in the range $-40°$ C. to $-120°$ C.

The labelling reagent may be attached to sites on the carbohydrate substances, after release if necessary from an attached biomolecule. Alternatively, the biomolecule may be modified in known way to enable incorporation of the labelling reagent.

A carbohydrate substance may be labelled with a labelling reagent much as ANTS, ANSA or ANDA by incubating the substance with the labelling reagent and e reducing agent, e.g. sodium cyanoborohydride. The sodium cyanonborohydride is conveniently in solution in dimethylsulphoxide (DMSO). For good labelling it is found useful to add the labelling reagent in solution in a mixture of acetic acid and water, e.g. containing 15 parts by volume of acetic acid to 85 parts by volume of water.

The rate of migration of substances undergoing electrophoresis varies with the size (molecular weight) and structure of the substances. The invention may thus be used to obtain information on the size and shape of carbohydrate substances, and by comparing results with those for known standards it may be possible partly or fully to characterise an unknown carbohydrate substance. One use of the invention is in elucidating carbohydrate structures, as described in WO88/10422, by cleaving an unknown carbohydrate into smaller fragments by use of glycosidases and identifying the resulting fragments.

Very good resolution of different carbohydrate substances has been obtained by the method of the invention; particularly using the preferred ANTS, ANSA and ANDA labels. For example, using ANTS glucose and all of its alpha 1-4 linked oligomers from maltose to maltoheptose can be well distinguished from each other. Further, some monosaccharides of the same molecular weight but of different structure can be distinguished from each other: for instance, glucose (Glc) can be distinguished from galactose (Gal), and 6-deoxyGlc from 2-deoxyGlc. Maltose can be separated from cellobiose, and maltotriose from cellotriose.

Further, certain mono-and disaccharides have been resolved into distinct groups via electrophoresis by using the ANSA label. The monosaccharides include glucuronic acid, iduronic acid and galacfuronic acids. The disaccharides include:

2-acetamido-2-deoxy-3-0 (betaD-gluco-4-ene pyranosyluronic acid)-D-galactose;
2-acetamido-2-deoxy-3-0 (betaD-gluco-4-ene pyranosyluronic acid)-4-0-sulpho-D-galactose; and
2-acetamido-2-deoxy-3-O (betaD-gluco-4-ene pyranosylurnoic acid)-6-0-sulpho-D-galactose.

Very good sensitivity can also be achieved with the method of the invention. For instance, using the ANTS label material present in concentrations as low as 1.0 pmol has been detected using a UV light box for viewing, while concentrations down to 0.2 pmol have been detected using a CCD and better sensitivity may be obtained under optimum conditions.

The invention is applicable to use on a wide range of carbohydrate structures, including those derived from glycoproteins, proteoglycans, glycolipids, glycosphingolipids, polysaccharides, glycosaminoglycans and other biomolecules, including complex biomolecules containing any of these as a component.

The invention will be further described, by way of illustration, in the following detailed description which refers to the accompanying drawings, in which:

FIG. 14 is the abreviated structural formula of a complex branched oligosaccharide re[erred to herein as oligosaccharide III;

Figure 15:
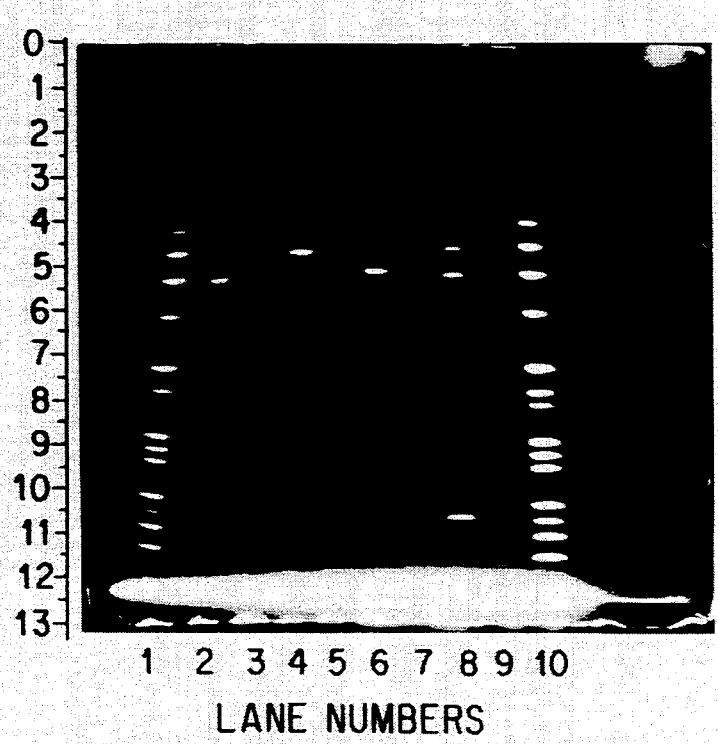
Figure 16:
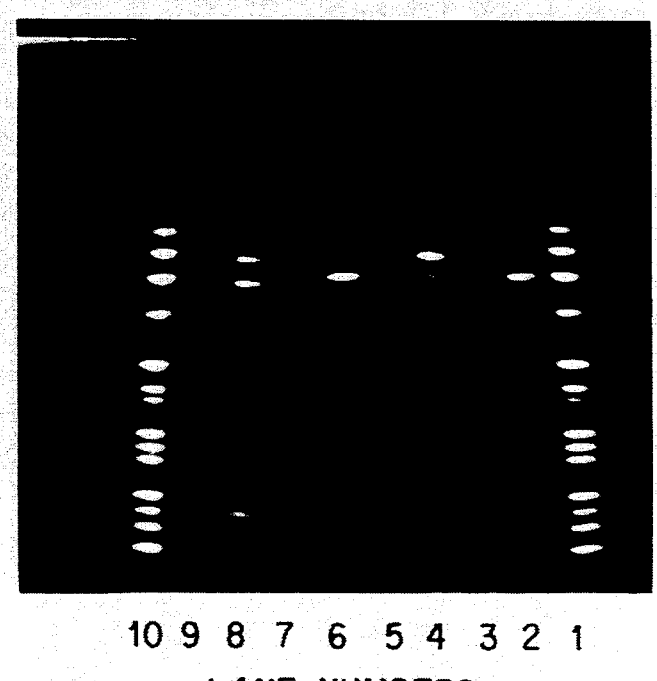

FIG. 15 is a photograph of a fluorescent electrophoretogram of reducing saccharides derivatised with ANTS, showing results for a standard mixture and also the products of the digestion of oligosaccharide III with two glycosidases; and FIG. 16 is an image of a fluorescent electrophoretogram of reducing saccharides derivatised with ANTS, obtained from the graphics display of a cooled CCD imaging system.

DETAILED DESCRIPTION OF EMBODIMENTS

Example 1

Materials

ANTS was obtained from Molecular Probes Inc. as its disodium salt. Heat hydrolysed wheat starch and the saccharides shown in Table 1 were obtained either from Sigma Chemical Co. Ltd. or from Aldrich Chemical Co. Ltd. The oligosaccharide I and II shown in FIGS. 5 and 6 were a gift from of Dr J. C. Klock. "Electran" or analytical grade reagents were used for the elctrophoretic and derivatisation procedures and were obtained from BDH Ltd. or from Sigma Chemical Co. Ltd. Alpha-amylase (EC 3.2.1.1.) from *Bacillus subtilis* was obtained from Boehringer Mannheim and beta-galactosidase (EC 3.2.1.23) from *Escherichia coli* was obtained from Sigma Chemical Co. Ltd. Uniformly labelled $^{14}$C-glucose (10.0 GBq/mmol) was obtained from Amersham International plc.

Fluorescent Labelling

Figure 1:
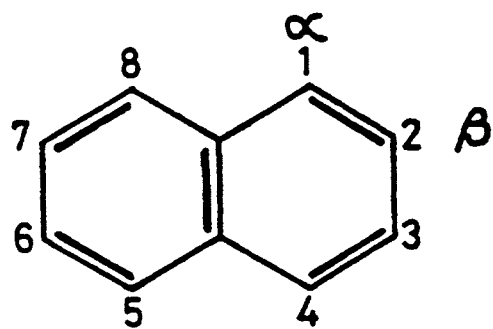
FIG. 1 illustrates the structure naphthalene.
Figure 2:
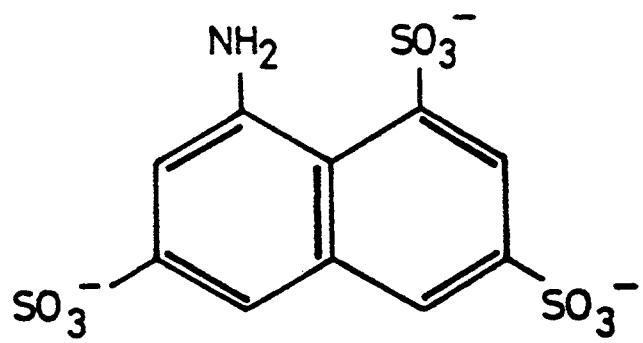
FIG. 2 illustrates the structure of ANTS, shown in ionized conditions.
Figure 3:
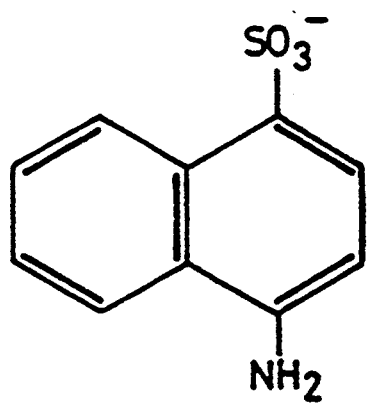
FIG. 3 illustrates the structure of ANSA, shown in ionized condition.
Figure 4:
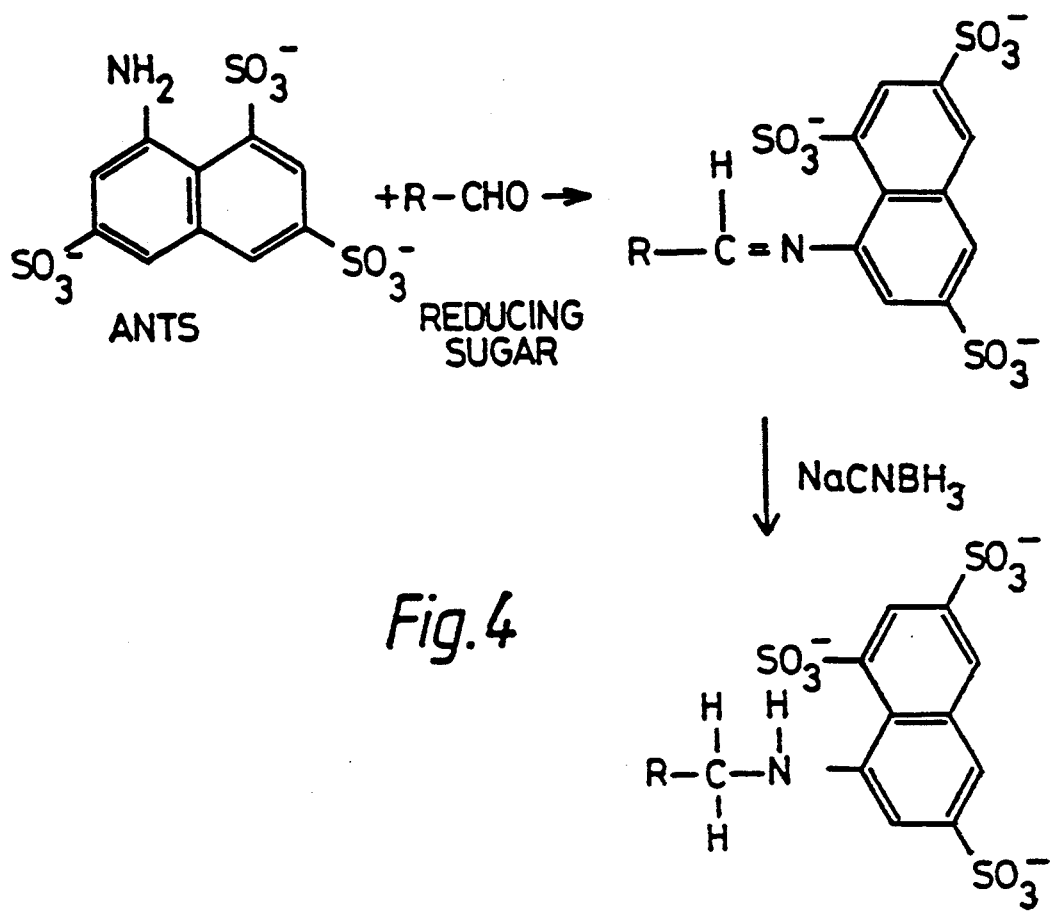
FIG. 4 is an equation illustrating the reaction of ANTS with a reducing sugar.

FIG. 4 illustrates the reaction of ANTS with a reducing sugar, resulting in the sugar being labelled with ANTS at its reducing end.

The standard method for reacting saccharides with ANTS was as follows. Suitable volumes, usually 5 ul or 10 ul, of 1 mM saccharide solutions in water were placed in microcentrifuge tubes and freeze-dried using a centrifugal vacuum evaporator (c.v.e.) (Gyrovap, V.A. Howe Ltd.). To each dry sample was added 5 ul of 0.2 M-ANTS solution in glacial acetic acid/water (15:85,v/v) and 5 ul of 1.0 M-sodium cyanoborohydride (NaCNBH$_3$) solution in dimethylsuphoxide (DMSO). The solution was vortex-mixed, centrifuged briefly at 10,000 g to ensure all the reactants were in the tips of the tubes and incubated at 37° C. for 15 h. The reaction mixture was dried under vacuum for 4 h in a c.v.e. at approximately 45° C. and dissolved in a suitable volume of electrophoresis sample buffer, so that the concentration of each labelled saccharide was 100 pmol/ul. Labelled sacchardides were stored at −70° C.

The standard method was varied to determine the optimal reaction conditions. In these reactions glucose, lactose and maltopentaose were derivatised together as test saccharides. The quantities of saccharides, the concentration of ANTS and acetic acid and the reaction time were all the varied as indicated. The volumes of the ANTS and NaCNBH$_3$ solutions the concentration of NaCNBH$_3$ and the temperature were kept constant unless otherwise stated.

Enzymological Digestions

Heat hydrolysed wheat starch was suspended, with vigorous mixing, at a concentration of 10 mg/ml in 0.1M-ammonium acetate buffer pH 5.5 at 37° C. To 50 ul of this suspension was added 5 ul of a solution containing 0.75 ug/ml of alpha-amylase form *B. subtilis*. The mixture was incubated for 30 mins at 37° C. when the digestion was stopped by the addition of 1 ml of ice-cold ethanol and dried under vacuum using a c.v.e. The digestion products were reacted with ANTS using the standard conditions described above, and dissolved subsequently in 50 ul of electrophosresis sample buffer. 2.0 ul was analysed per gel lane.

The oligosaccharides I and II were both treated with beta-galactosidase and then reacted with ANTS as follows. To approx 2 nmol of each oligosaccharide in solution in 5 ul of 0.1 M-Naphosphate buffer pH7.4 at 37° C. was added 1 ul of a solution of beta-galactosidase in water (1 unit (suppliers definition) /ml). The mixture was incubated for 4 h at 37° C. and then freeze dried in a c.v.e. The dry digest was derivatised with ANTS using the standard conditions. Controls containing either no oligosaccharide or no enzyme were carried out simultaneously. Each enzymic digestion and the subsequent derivatisiaation were carried out in the same reaction tube.

Electrophoresis

Saccharides labelled with ANTS were subjected to polyacrylamide gel electrophoresis (PAGE) using a type SE600 electrophoresis apparatus from Hoefer Scientific Instruments Ltd. The plates of the gel cassettes were made either of window glass when the gels were to be photographed, or of Pyrex glass when gels were imaged in vitro using a CCD-camera.

The electrophoretic buffer used was based on the Tris-HCl/Tris-glycine discontinous system of Laemmli (1) but the detergent sodium dodecyl sulphate (SDS) was omitted throughout. The polyacrylamide gel consisted of a linear gradients from 20% w/v to 40% w/v acrylamide containing 0.53% w/v to 1.06% N,N′-methylenebisacrylamide (bis), respectivley, as cross-linker. The gradient was generated using a 3-channel peristaltic pump. The polymerisation of the gel was initiated by the addition of 20 ul of 10% w/v ammonium persulphate solution and 10 ul of N,N,N′,N′, tetramethylene diamine (TEMED) per 12 ml of each gel solution. The resolving gel size was 140 mm high by 140 mm wide by approx. 0.5 mm thick. A moving boundary (stacking) buffer system was used to give sharp bands and high resolution. The sample wells were 4 mm wide. Samples were electrophoresed at 100 V for 30 min, 500 V for 30 min and finally at 1000 V for approx. 120 min, until the buffer front reached to approx 5 to 10 mm from the gel bass. All the voltages were held constant. The gels were cooled to 5° to 7° C. by the surrounding stirred lower electrode buffer.

Photography

Gels were photographed after removal from their cassettes and placing on a u.v. light box (Transilluminator, type TM40, UVP Ltd.) with a maximum emission wavelength of 302 nm and a power of approx, 7000 uw/cm². A Polaroid type 55 film (ISO 50), which gave both a negative and positive photograph, a Wratten 8 gelatin filter (Kodak), an aperture of f4.5 and time of 50 sec were used. The photographic images were approximately 62% of the size of the original gel.

Densitometry

Film negatives were scanned with white light on a Chromoscan 3 densitometer (Joyce Loebl Ltd, Gateshead, U.K.) using a slit size of 0.1×1.5 mm, except when generating the densitometric profile shown in FIG. 9 in which the slit size was 0.05×1.5 mm. Densitometric measurements of the bands produced by the fluorescently labelled saccharides were carried out as described previously (reference 2). All the absorbance measurements were less than 85% of the maximum film density.

Quantitation of the Fluorescent Labelling Using $^{14}C$ Glucose

ANTS was reacted with various quantities of glucose varying from 14 nmol to 110 nmol per reaction tube, each containing 0.5 uCi of uniformly labelled $^{14}C$-glucose. After drying the reaction mixture was dissolved in 100 ul of water and 1.0 ul was applied to a silica gel thin layer chromatography (t.l.c.) plate (Polygram SILG, 20 cm×20 cm, (Macherey-Nagel)) and chromatographed in a solution of butan-1-ol/ethanol/water, (5:3:2, by vol.). The chromatogram was autoradiographed using Cronex 4 X-ray film (Du Pont). Known quantities of unreacted $^{14}C$-glucose were chromatographed as standards.

Time-course Measurement for the Fluorescent Labelling 25 nmol of each of the saccharides glucose, lactose and maltopentaose were reacted together at 37° C. with 20 ul of 0.2 M-ANTS in glacial acetic acid/water (15:85,V/V) and 20 ul of 1.0 M-NaCNBH₃ in DMSO. Samples (4.0 ul) were removed at intervals, frozen immediately in liquid $N_2$ until the last sample had been taken. All the samples were dried together for 4h at approximately 45° C. in a c.v.e, disssolved subsequently in 40 ul of electrophoresis sample buffer and 2.0 ul was electrophoresed. The extent of the reaction was determined by densitometry of the labelled saccharide bands in the film negative of the gel.

Gel Imaging Using a Cooled CCD

Gels were imaged elctronically without removal from their electrophoresis cassettes using an Astromed 2200 Imaging system (Astromed Ltd, Cambridge, U.K.). Briefly, except for production of the image of FIG. 9a, the system consisted of a cooled CCD, containing an array of 385 by 578 picture elements (pixels) each having dimensions 22×22 um, onto which was focused an image of a section of the gel. The gel image was demagnified fivefold by a lens with an aperture of f1.9. The CCD was cooled to approximately 242° K. by a Peltier cooler.

Each gel was viewed in 6 sections and the images joined by an associated computer to give an image of a total area of gel approximately 120 mm square. The time for viewing each section of each individual gel was constant for individual gels but was varied from gel to gel, being either 10 sec or 60 sec. The CCD response was directly proportional to the imaging time. The illumination was in the plane of the gel from the anodic edge using a fibre optic light guide with the dimensions 0.5 mm×200 mm. The light guide was adjusted so that its aperture was aligned with the gel edge. The gel cassette was placed so that it abutted the light guide. The light source was a 100 W tungsten-halogen lamp. The excitation and emission interference filters (Omega Inc.) had transmission maxima of 390 nm and 492 nm, respectively. In the case of images taken for the quantitative data any unevenness in the gel illumination was removed digitally using as a reference an image of a gel containing uniformly 0.1 mM ANTS.

The fluoresence of the saccharide bands in the gels was measured by determining the mean number of photons registered per pixel per minute in a defined rectangular area 40×20 pixels, covering each band and subtracting the gel background measured on similar adjacent blank areas in the same gel lane.

Figure 9A:
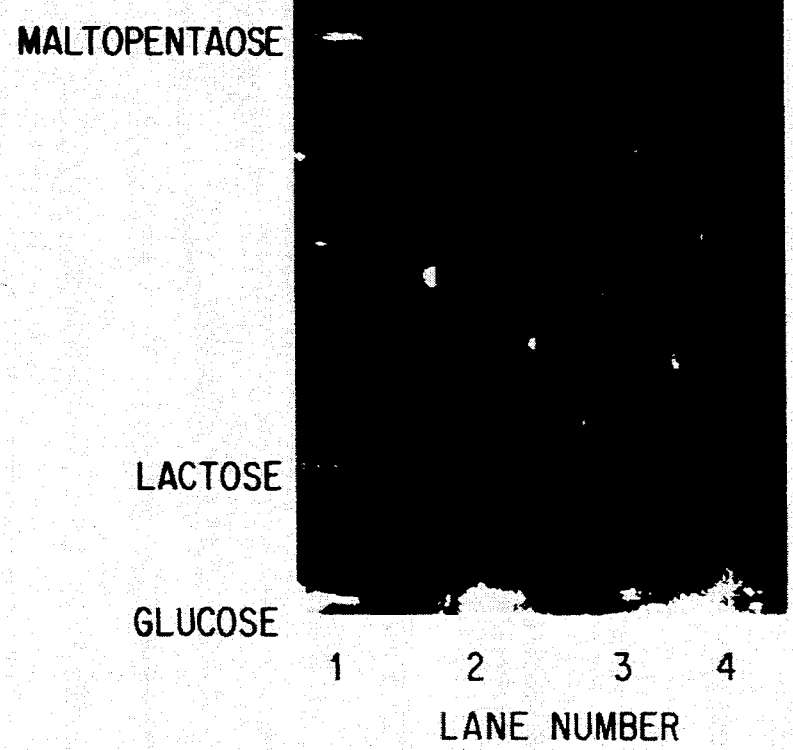
FIGS. 9a and 9b are photographs of the graphics display of a coo ed CCD imaging system, illustrating the lowest limits of detection.

The image shown in FIG. 9a was obtained by a slightly more sensitive system that that described above. The essential differences were that the lens aperture was f1.2, the light guide had exit dimensions 0.5 mm×90 mm and a 50 W light source was used. Since the light guide was less wide that the gel, the latter was positioned before it mechanically on a precision carriage controlled by the computer system.

Results

Derivatisation of the saccharides with ANTS

Various reaction conditions were altered to determine the optimal labelling with ANTS of the three chosen test saccharides, glucose, lactose and maltopentaose. The effect of varying the acetic acid concentration between zero and 20% (v/v) in the standard method was measured. When the concentration of acetic acid was between 5 and 20% (v/v) the degree of derivatisation was optimal and constant. When the acetic acid concentration was zero the degree of derivatisation was approximately 84% of the optimum. A solution of glacial acetic acid/water (15:85,v/v) was chosen for the standard conditions. It was found convenient to dissolve the ANTS in this solution for which gentle warming was required. The time course for the reaction of ANTS with equimolar amounts of the three test saccharides was measured. The time courses for all three saccharides were similar. The reaction was virtually complete by 12h at 37° C. and a time of 15h was used for the standard conditions.

The extent of saccharide derivatisation was measured as the concentration of ANTS was varied in the standard method. When 25 nmol of each test saccharide was reacted the maximum derivatisation was obtained when the concentration of ANTS was at least 0.1M, and a concentration of 0.2M was used routinely. Similar results were obtained for each saccharide tested and also when the quantity of each was reduced to 2.5 nmol per reaction tube.

Densitometric measurements of the autoradiographs of the t.l.c. analyses of the reaction products of the ANTS labelling of $^{14}C$-glucose showed that, for all the quantities of glucose tested, greater than 99% had been reacted and that 92% occurred in a new band, which for the higher loadings of glucose could be seen to be fluorescent when the t.l.c. plate was illuminated by u.v. light. A faint background of radiolabel was found along the length of each sample lane which accounted for the remaining 8% of the label not in the major band. This may have been caused by either impurities in the ANTS or the glucose or by artefacts of the reaction or the chromatography.

Quantitative Analysis and Limits of Sensitivity

Figure 7:
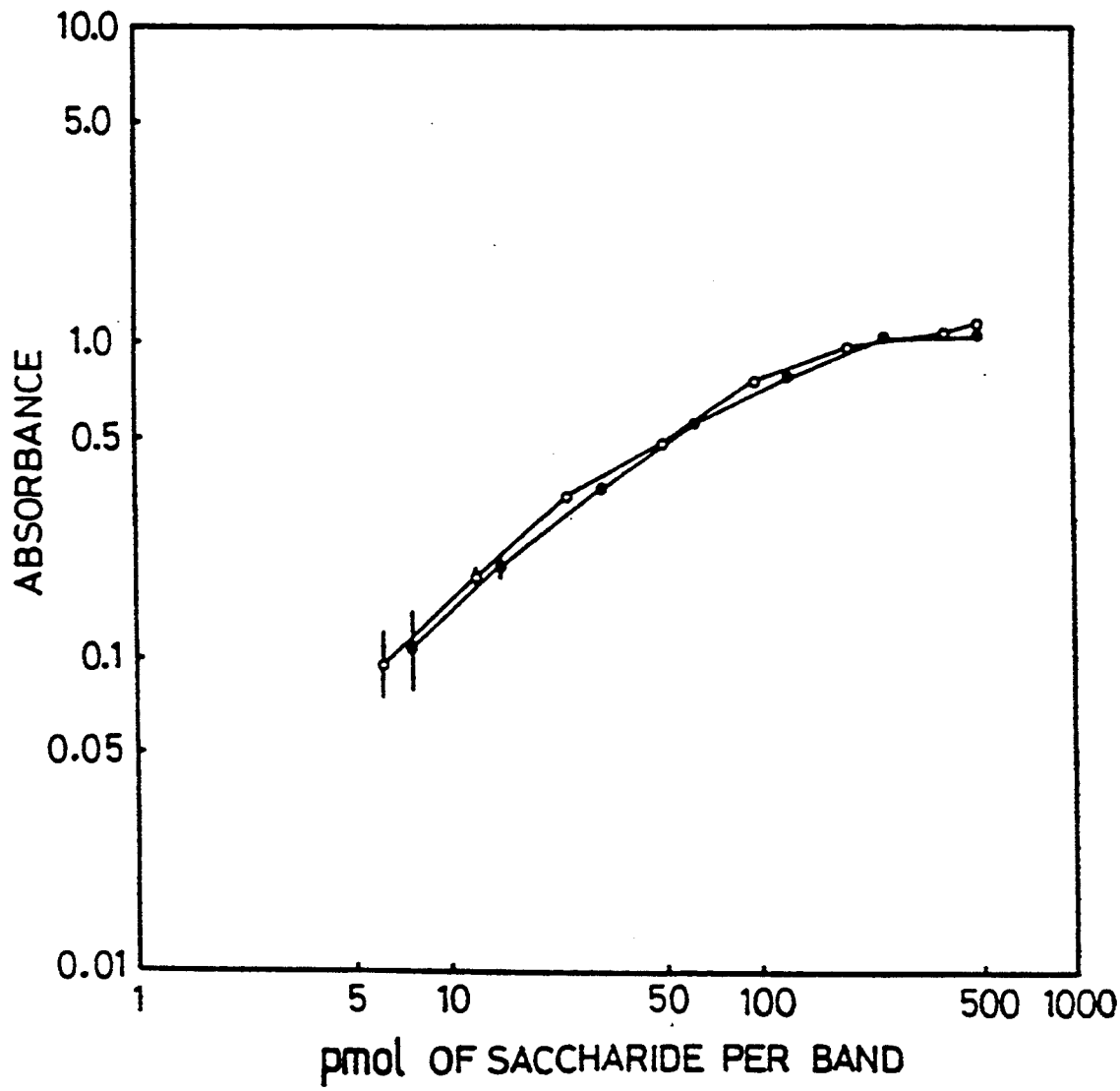
FIG. 7 is a graph of absorbance versus quantity of saccharide, illustrating the variation of film response with the quantity of ANTS-labelled saccharide per gel band.

The quantitative characteristics of the photographic recording method were determined by derivatizing together 25 nmol of each of the three test saccharides using the standards conditions, dissolving the reactions products in 100 ul of electrophoresis sample buffer, serially diluting the solution and analysing by PAGE 2 ul of each dilution. The film response for ANTS labelled maltopentaose is shown in FIG. 7, where the data are plotted on logarithmic scales to encompass conveniently the wide dilution range. In FIG. 7 the open circles represent the film absorbances for samples of maltopentaose treated in this way. As can be seen, the film response varied non-linearly linearly with the quantity of saccharide and decreased markedly when the higher dilutions were analysed.

The filled circles in FIG. 7 represent the film absorbances for samples in which the quantities of the three test saccharides in each reaction were varied between 0.39 nmol and 25 nmol and a fixed proportion, 1/50, of each reaction mixture was electrophoresed. Similar film responses were obtained in this case.

In FIG. 7, each point represents the mean of four determinations for the derivatisation of maltopentaose. The standard error is shown for the lowest two points on each. The rest of the standard errors of the mean were all less than 5%.

The data for glucose and lactose are not shown but were similar.

Although quantities of saccharides as low as 1 pmol could be detected faintly by eye on the film it was not found possible to measure accurately the film absorbance at levels below approximately 5 pmol of saccharide per band.

A similar experiment was carried out in which the saccharide content of the reaction was varied but in this case the reaction mixture was dissolved in varying volumes of electrophoresis buffer so that the concentration of each of the three test saccharides was 100 pmol/ul. When 2 ul of each solution was electrophoresed and the fluorescence measured it was found that the film response was constant, that is, independent of the quantity of saccharide in the reaction tubes. This result is in agreement with the data from the radiolabelling experiment which showed that the degree of labelling of glucose was constant irrespective of the quantity in the reaction tube, up to the maximum of 110 nmol.

The quantitive characteristics of the CCD imaging system were determined by electrophoresing samples serially diluted from a reaction containing 25 nmol of each of the test saccharides as described for assessing the photgraphic method. The gels were imaged for either 10 sec or 60 sec. and the results normalised to 60 sec. The results are shown in FIG. 8, with the filled circles representing the mean valves for maltopentaose for the range 3.1 to 500 pmol.

Figure 8:
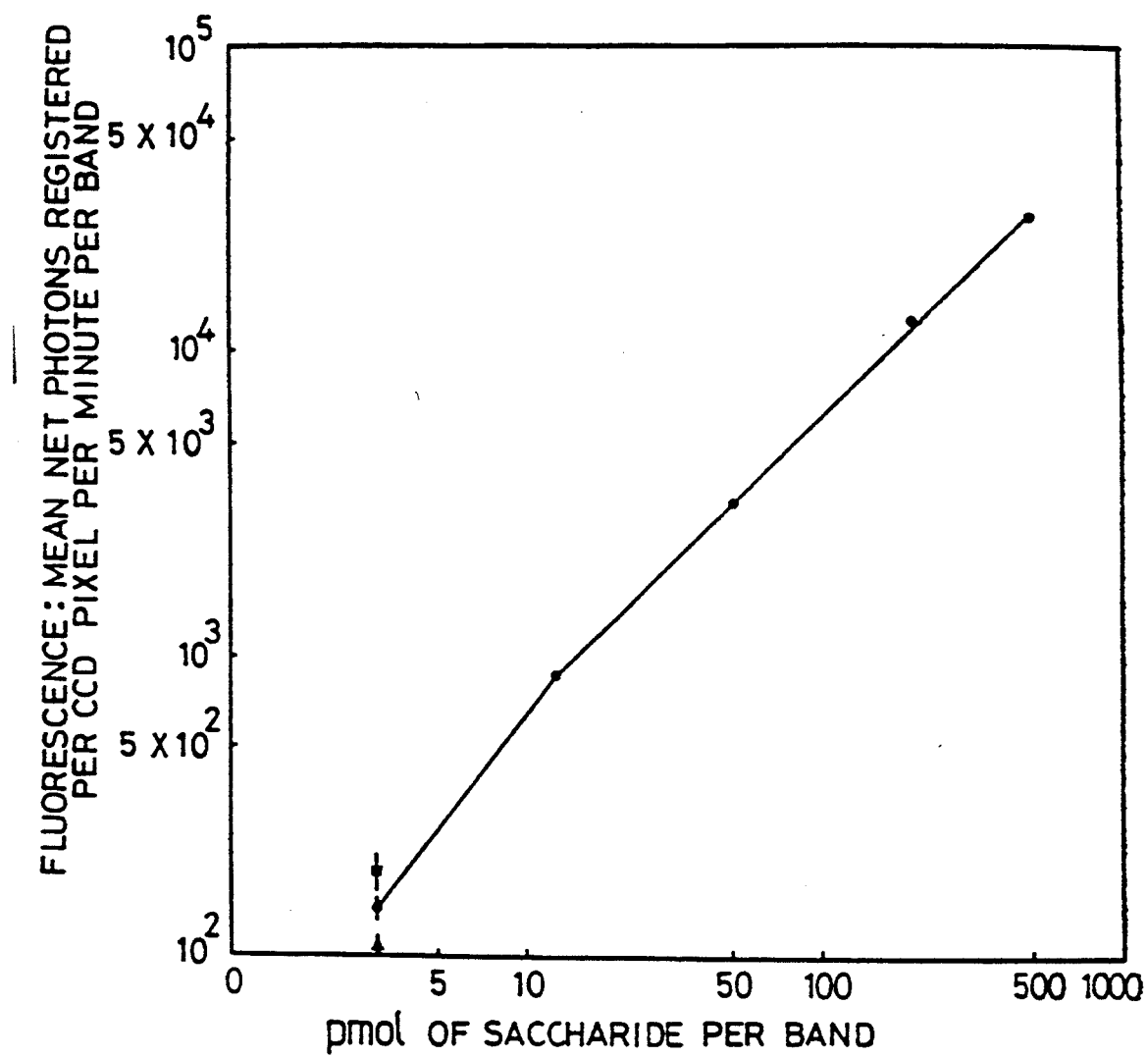
FIG. 8 is a graph of fluorescence versus quantity of saccharide, illustrating the variation of CCD response with the quantity of ANTS labelled saccharide per gel band.

The values for glucose and lactose were similar to those for maltopentaose for each of the four highest loadings: for reasons of clarity these results are not shown in FIG. 8. The standard errors of the means were all less than 5.1% unless indicated. For the lowest quantity of saccharide (3.1 pmol) there was considerable variation in the means and standard errors and these are shown for all three test saccharides, with the filled square representing glucose and the filled triangle lactose.

The CCD responded linearly from 12.5 to 500 pmol and the standard error for each value was less than 5.1%. The data for glucose and lactose were similar for the range 12.5 to 500 pmol. However considerable variation between the individual saccharides and relatively high standard errors were found for the 3.1 pmol quantity. This reflected the difficulty of obtaining accurate measurements when the signal from the saccharide band was close to the gel background. However it was possible to visualise lower quantities.

Figure 9B:
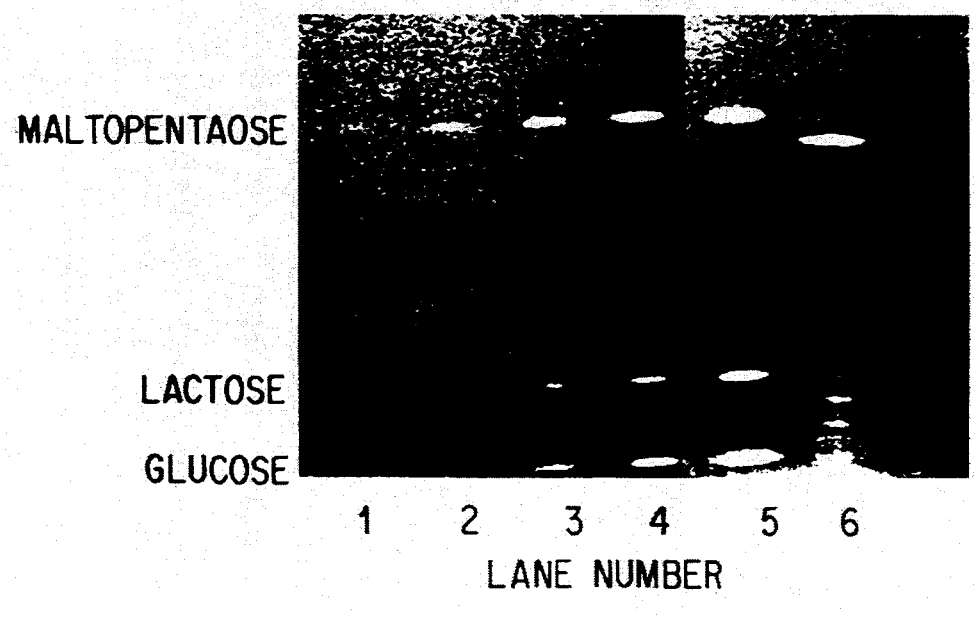

FIGS. 9a and 9b show CCD images of relevant sections of gels on which have been run serial dilutions of a sample containing equimolar quantities of the three test saccharides. In both images the contrast has been optimised. Each lane, except FIG. 9b, lane 6, contained equimolar quantities of ANTS-labelled glucose, lactose and maltopentaose serially diluted from a standard reaction mixture containing 25 nmol of each saccharide. The samples were loaded in alternate gel lanes. The sample buffer showed no fluorescent bands.

For FIG. 9a, the gel was imaged using a f1.2 lens, a 50 W lamp and a 0.5 mm×90 mm light guide. Lane 1, 0.8 pmol; lane 2, 0.4 pmol; lane 3, 0.2 pmol; lane 4, 0.1 pmol. The sharp horizontal discontinuity in the background is a join between two image sections. This image was processed digitally to smooth the background.

For FIG. 9b, the gel was imaged using the standard viewing system. Lane 1, 0.4 pmol; lane 2, 0.8 pmol, lane 3, 1.0 pmol; lane 4, 2.0 pmol; lane 5, 4.0 pmol; lane 6, 2% of the standard reaction mixture. Only that section of the lane having significant fluorescent background is shown. The vertical discontinuity in the background between lanes 4 and 5 is the Join between two image sections. It was possible to detect as little as 0.2 pmol per band when using a 60 sec viewing time (see FIG. 9a, lane 3). The level of background obtained when loading 2% of a standard reaction solution containing no saccharides is also shown in FIG. 9b.

Electrophoretic Analysis

Figure 10:
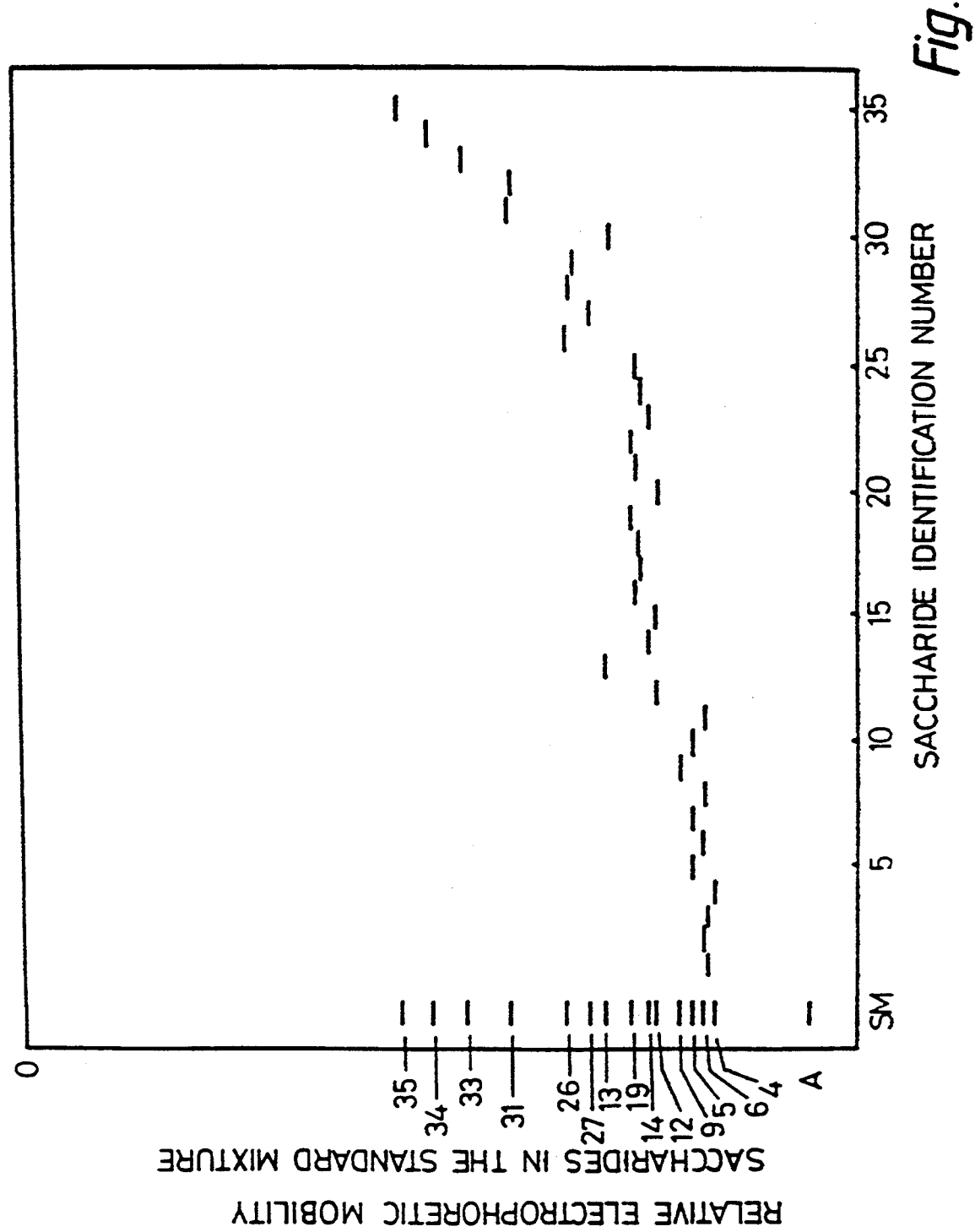
FIG. 10 is a diagrammatic representation of an electrohoretogram of ANTS derivatised saccharides showing their relative electrophoretic mobilities.

A diagramatic representation of an electrophoretogram depicting the separation of 35 different ANTS labelled saccharides is shown in FIG. 10.

In this Figure each band represents the position of an individual saccharide relative to unreacted ANTS (labelled A) which moved at the buffer front. Each gel track number corresponds to the number of each saccharide shown in Table 1. The track labelled SM shows the separation of the standard mixture of 14 saccharides chosen to give a wide spread of well resolved bands. In order of decreasing mobilities the identities of the bands are, (4), 6-deoxyglucose, (6) glucose, (5) galactose, (9) N-acetylgalactosamine, (12) galactosylgalactose, (14) lactose, (19) maltose, (13) galactobiose, (27) cellotriose, (26) maltotriose, (31) maltotetraose, (33) maltopentaose, (34) maltohexaose, (35) maltoheptose. (The numbers is parentheses refer to Table 1.) The top of the resolving gel is marked by a "O".

It can be seen that as the size of the saccharides increases there is a general reduction in electrophoretic mobility. However numerous saccharides with identical molecular weights were well separated. The most notable separations were as follows, 6-deoxyglucose had the highest mobility of all the saccharides tested and was separated clearly from the three other deoxyhexoses. The epimers glucose and galactose were well resolved but mannose and galactose were not. N-acetylgalactosamine and N-acetylglucosamine were resolved but the latter had the same mobility as galactose.

The dissaccharides tested also had a range of mobilities. The isomers galactosylgalactose and galactobiose were resolved, as were maltose, isomaltose and cellobiose. By contrast the corresponding 1-3 linked disaccharides, nigerose and laminaribiose, and the 1-6 linked disaccharides isomaltose and gentiobicse had different mobilities but were not well resolved.

The trisaccharides tested also showed a range of mobilities. Maltotriose had a slightly lower mobility than isomaltotriose and was well resolved from cellotriose. Maltotriose also had a slightly lower mobility than panose but they were not well resolved. Similarly maltotetraose had a small mobility difference from alpha-D-Glc-(1-6)-(alpha-D-Glc-(1-4)-)$_2$-D-Glc.

The 14 saccharides which were in the standard mixture (SM) shown in the left hand track of FIG. 10 were chosen to give a wide spread of well resolved bands. The mixture included glucose and all the (1-4) linked straight chain oligomers of glucose from maltose to maltoheptaose.

Figure 11:
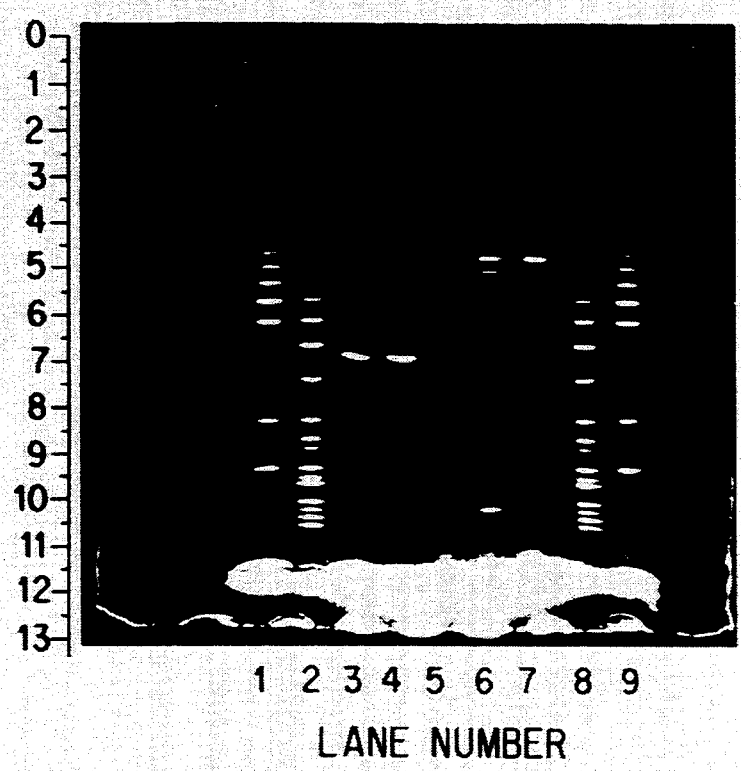
FIG. 11 is a photograph of an electrophoretogram of various ANTS derivatised saccharides.

This standard and various other sugars, all labelled with ANTS, were run on an electrophoretic gel and a photograph of the resulting electrophoretogram is shown in FIG. 11. In this Figure the lanes are as follows: Lanes 1 and 9, partial alpha-amylase digest of the equivalent of 20 ug of heat hydrolysed wheat starch; lanes 2 and 8, the standard mixture with each band representing approximately 200 pmol of each derivatised saccharide. In order of decreasing mobilities the identities of the bands are, 6-deoxyglucose, glucose, galactose, N-acetylgalactosamine, galactosyl-galactose, lactose, realrose, galactobiose, cellotriose, maltotriose, maltotetraose, maltopentaose, maltohexaose, maltoheptaose; lane 3, oligosaccharide I; lane 4, oligosaccharide I treated with beta-galactosidase; lane 5, beta-galactosidase; lane 6, oligosaccharide II treated with beta-galactosidase; lane 7; oligosaccharide II. The strongly fluorescent band at the base of the gel is caused by excess ANTS. The conditions used for the enzyme digestions and the ANTS derivatisations are described above. One tenth of the total reaction mixture was analysed for each sample in lanes 3 to 7.

The results in FIG. 11 indicate the range of the resolving power of the method used. In lanes 1 and 9, which contain the ANTS-derivatised partial alpha-amylase digest of heat hydrolysed wheat starch, seven bands can be seen to correspond to glucose and its (1-4) linked straight chain oligomers up to maltoheptaose. In addition there are 19 other bands having lower mobilities than maltoheptaose each resolved from the next. Presumably these represent individual polysaccharides differing from one another by a single hexose unit. A number of additional minor bands exist which may represent oligosaccharide containing (1-6) linkages which are not cleaved by the alpha-amylase.

Figure 12:
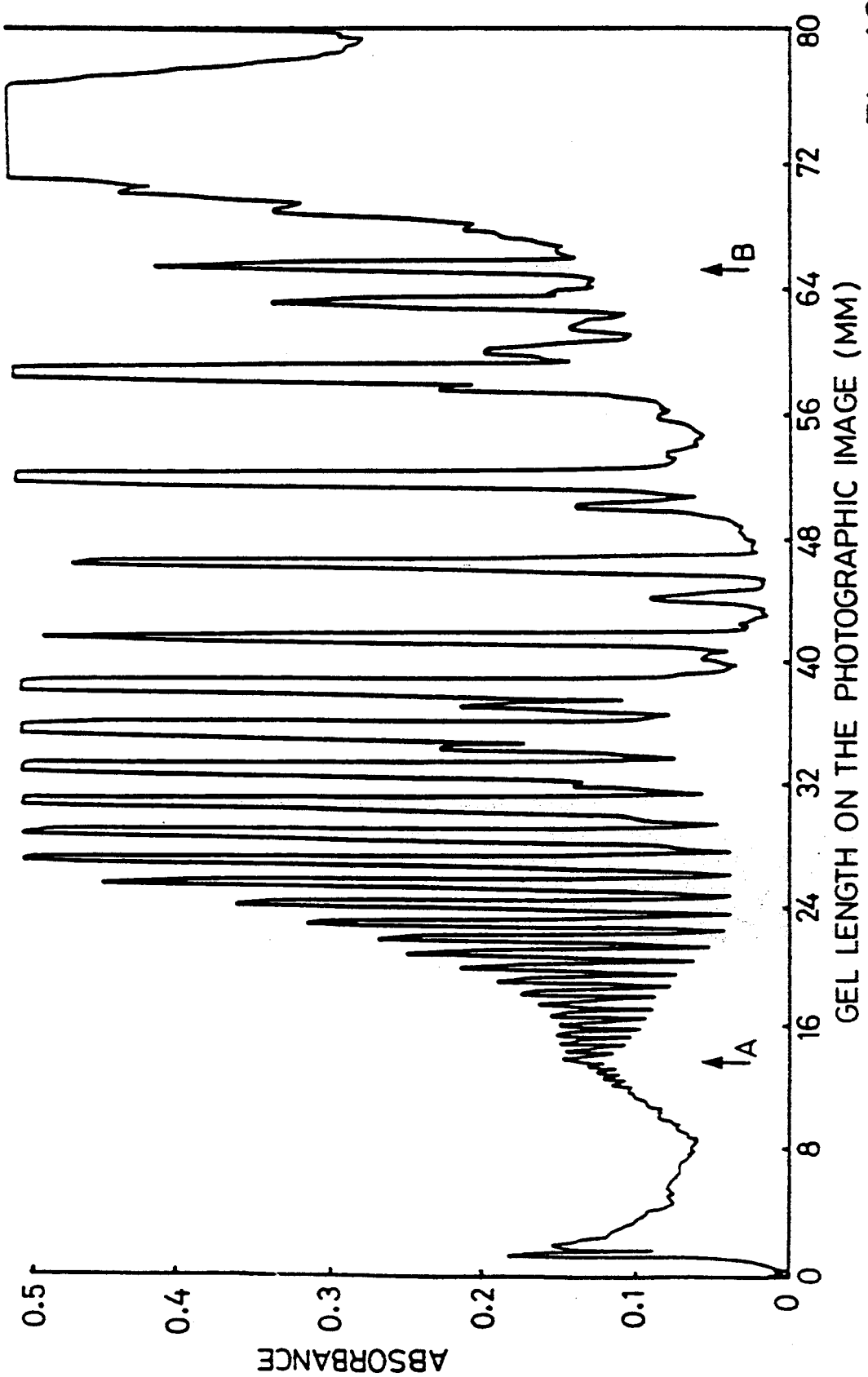
FIG. 12 is a densitometric profile of a photographic nags, tire of a polyacrylamide gel electrophoresis separation of an ANTS derivatised alpha-amylase partial digest of heat hydrolysed wheat starch.

In FIG. 12 is shown a densitometric trace of lane 1 from FIG. 11. The profile was obtained by scanning lane 1 of the negative of the photograph shown in FIG. 11. The densitometer slit size was 0.05×1.5 mm. The arrow marked A indicates the position of the 26th major band from the glucose band which is indicated by the arrow marked B. The resolution of each band up to 26 hexose units can be seen clearly and there is also an indication that even higher molecular weight polymers can be resolved.

Figure 5:
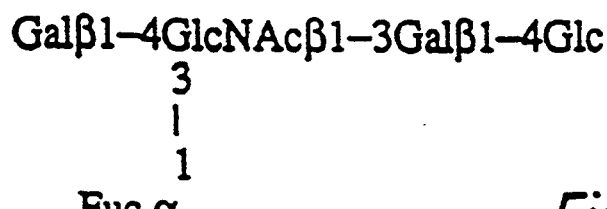
FIG. 5 is the abbreviated structural formula of a complex branched oligosaccharide referred to herein as oligosaccharide I.
Figure 6:
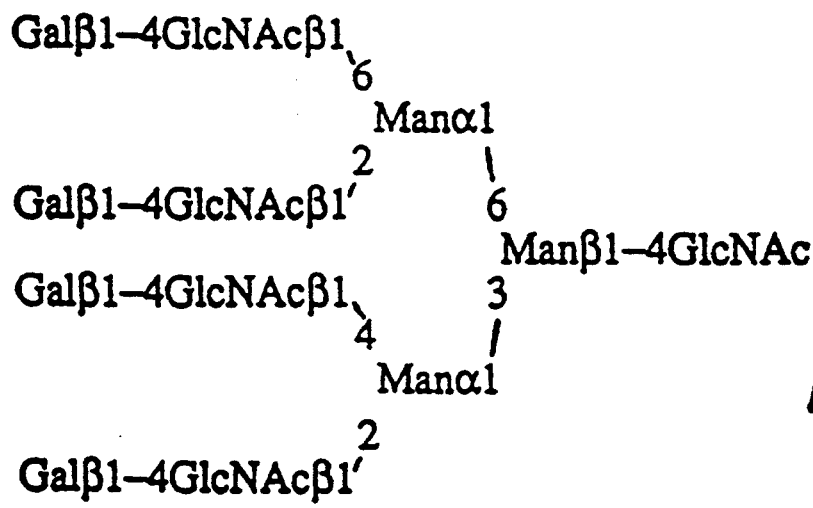
FIG. 6 is the abbreviated structural formula of a complex branched oligosaccharide referred to herein as oligosaccharide II.

Lane 3 and 6 in FIG. 11 contained the complex oligosaccharide I and II, respectively (see FIGS. 5 and 6). They both had higher mobilities than the oligosaccharidse containing a similar number of glucose residues. Oligosaccharide I had a mobility between maltotetraose and maltopentaose and oligosaccharide II had a mobility between those of the ninth and tenth major bands in the starch digest lanes.

Lanes 4 and 6 in FIG. 11 show the effect of treating the oligosaccharide I and II with beta-galactosidase. Oligosaccharide I remained undigested. Oligosaccharide II was partially digested. Three bands with lower nobilities than the original were produced. The two closest to the original band appear to represent oligasaccharide products which have lost one or more galactose residues. The third band has the same mobility as the galactose standard and represents the cleaved galactose. A control reaction containing only beta-galactosidase is shown in lane 5. Several faint artefactual bands having mobilities higher than maltotriose can be seen in tracks 3 to 7. These bands could be seen in all samples including those which contained no enzymes or saccharides. They only became significant when a relatively high proportion of the reaction mixture was anlysed (10% in lanes 3 to 7 in FIG. 11. See also FIG. 9b). In lanes 3 to 7 in FIG. 11 there was also a faint sharp band which moved slightly faster than oligosaccharide I. This band, of unknown identity, was also present in all samples and could be seen if sufficient was loaded. It can be seen most clearly in FIG. 9b, lane 6. It has a lower emission wavelength an the ANTS. It appears that the beta-galactosidase (see lanes 4 and 5, FIG. 11) contained traces of galactose or a contaminant with a similar mobility.

Figure 13:
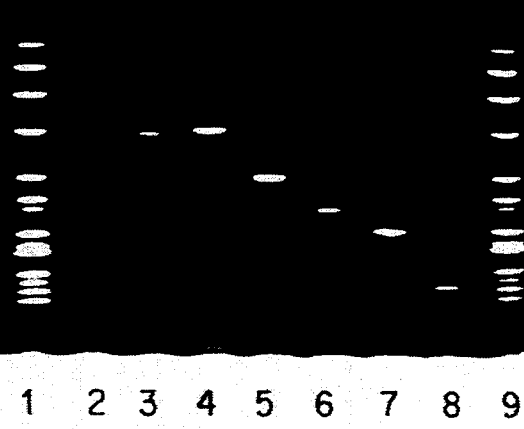
FIG. 13 is a photgraph of the graphics display of a cooled CCD imaging system showing an electrophoretogram of various ANTS derivatised saccharides.

In FIG. 13 is shown a photograph of the graphics display of an image of a gel showing a typical separation of a variety of oligosaccharide and the standard mixture. In this figure the lanes are as follows: lanes 1 and 9, the standard mixture. In order of decreasing mobility the identities of the band are 6-deoxyglucose, glucose, galactose, N-acetylgalactosamine, galactosyl-galactose, lactose, maltose, galactobiose, cellotriose, maltotriose, maltotetraose, maltopentaose, maltohexaose, maltoheptaose; lane 2, water; lane 3, Glc alpha 1-6 (Glc alpha 1-4) Glc; lane 4, maltotetraose; lane 5, panose; lane 6, N-acetylneuraminlactose; lane 7, isomaltose; lane 8, L-fucose.

Each band contained approx. 200 pmol of derivatised saccharide. The gel was imaged for 10 sec per section. The total image shown consisted of six sections which were merged by the computing system and then reproportioned to fill the display. The area of gel shown had the dimensions approximately 120 mm square. The whole width of the gel was illuminated along its length from its anodic edge which was approx. 12 mm from the lower edge of the image. The main broad band of excess ANTS is almost entirely outside the imaged area, but feint artefactual bands arising from the ANTS can be seen.

Some saccharide samples appeared to contain impurities. For instance the single faint band below the main band of isomaltose and the bands below the main band in lane 5 (N-acetylneuruaminlactose) were found consistently. In the latter sample, the lowest band has the same mobility as lactose. The band above it is of unknown origin but it is possible that it represents the proportion (15% w/w, manufacturers data) of the 2-6 linked N-acetyl neuraminlactose which was present in the sample.

Discussion

ANTS is a novel and useful reagent for covalent labelling of saccharides. The ANTS derivatisation imparts both charge and fluorescence to the saccharides enabling then to be both electrophoresed and detected, ANTS was found to be the most suitable of numerous fluorophores tested since it has a relatively high charge enabling rapid separations in particular of the larger oligoeaccharides. It also has a large Stoke's shift which facilitates the differential filtration of the excitation and emission wavelengths, thus improving the sensitivity by decreasing the detectable background fluorescence. The excitation wavelength maximum of 370 nm enables an inexpensive tungsten-halogen lamp illumination to be used and the yellowish emissions, wavelength maximum 515 nm, facilitates direct observation of the band pattern. This wavelength is also well suited for detection by the CCD, which is less efficient at detecting blue light.

The labelling procedure is simple to perform and uses inexpensive reagents which are available commercially, The 15h reaction can be arranged conveniently overnight, It may be possible to accelerate the procedure by raising the reaction temperature. The reaction products are relatively stable and may be stored for several weeks in solution in electrophoresis sample buffer at $-70°$ C. without apparent degradation.

The reaction conditions have been optimised so that the derivatisation was virtually quantitative for up to at least 110 nmol of saccharide per reaction tube. For optimal labelling DMSO was essential. When it was replaced by water the degree of labelling was reduced by approximately 20%. The effect of varying the concentration of $NaCNBH_3$ has not yet been investigated rigorously. If it was omitted derivatives were obtained which had diminished and blue fluorescence. These derivatives had slightly different mobilities from those obtained when $NaCNBH_3$ was included.

The relatively high concentration of ANTS, required for complete derivatisation, could be a disadvantage when small quantities of saccharides were being analysed. For instance, when the standard derivatisation conditions were used and 10% of the total reaction mixture was applied to the gel then faint artefactual bands arising from the ANTS were seen (see FIG. 11, lanes 3 to 7). These bands are also shown in FIG. 9b, lane 6 where 2% of a standard reaction mixture containing no saccharide was imaged at high sensitivity. To ensure that lower molecular weight saccharides can be detected against the artefactual bands it is necessary to react a minimum of about 100 pmol, and to load no more than 10%. The practical limits for the proportion of the standard conditions reaction mixture which could be loaded without causing gross distortions in the elctrophoresis band patterns was also about 10%. However, initial experiments show that it is possible to reduce the total reaction volume from 10 to 2 ul. It should be possible to reduce by 1/5 the total minimum quantity of any saccharide which can be treated and analysed as compared with the standard method described. The potential of the technique for the analsis of glycans was demonstrated clearly by the beta-galactosidase digestion of oligosaccharide II.

PAGE has been used previously for the separation of oligoeaccharides which are charged naturally (references 3, 4 and 5) and also for the separation of uncharged oligeaccharides as borate ion complexes (references 6). This latter method appeared to be of relatively low resolution and required radiolabelling of the oligosaccharide for their detection. In contrast, the PAGE method described here is of high resolution and avoids radiolabelling. In addition it has higher sensitivity than paper chromatography, t.l.c. and the non-capillary electrophoretic methods described previously for the analysis of small reducing carbohydrates. The limit of sensitivity of detection by the CCD is similar to that obtained for precolumn derivatisation high performance liquid chromatography (h.p.l.c.) methods, and better than that obtained for pulsed amperometric detection of underivatised saccharides, which has a sensitivity in the range 10 to 100 pmol (reference 7). The detector response of the latter method varies for each saccharide and requires calibration whereas the fluorescent labelling should give the same response per mole of reducing end group labelled and this was found to be so for the three saccharides tested rigorously. The resolving power approaches that of h.p.l.c. and capillary zone electrophoresis and is determined both by the size and structure of the saccharides. The wide range of molecular sizes which can be resolved is at least as good as that obtained by h.p.l.c. This separation range is in part owing to the use of a polyacrylamide gradient gel. However useful separations can also be obtained on uniform concentration gels (e.g. 30%, w/v). Small-scale gels have also been used successfully to obtain rapid analyses.

The method described has shown an unexpected resolution of some saccharides. The electrophoretic mobility was determined mainly by the size of the saccharides, but other factors appear to have an effect. The effective mass of each derivative, and thus its electrophoretic mobility, may, in part, be determined by the saccharide conformation and this may explain, for instance, the separation of maltose and cellobiose. However it seems unlikely that the effective masses of galactose and glucose differ significantly. The separation of these epimers could depend on a differential interaction of each saccharide with the gel matrix. At present the exact mechanism for the separations is unclear, and my be owing to a combination of the effects suggested.

Two methods of imaging the fluorescent electrophoretograms were used. The photographic method gave good quality negatives which enabled accurate densitometric measurement of the fluorescent gel bands, but the film response was non-linear. The limit of the film sensitivity was about 1 pmol per band using a 50 sec exposure time and an aperture of f4.5. This was also the limit of sensitivity when film exposures of 100 sec were used since the recorded background fluorescence increased to mask the increased band fluorescence. When gels were photographed a second time significant fading had occured. Densitometirc measurements were made on only the firs t exposure.

It has been shown previously that polyacrylamide gels can be imaged successfully using the Astromed 2200 cooled CCD system (2) and the present work demonstrates an additional application. The imaging was about 5 times more sensitive than photography, having a limit of detection of about 0.2 pmol. However visual inspection of the illuminated gels on the viewing platform of the imaging device showed that the CCD was at least 50 times more sensitive than the human eye. This contrasts with the photography to which the human eye had similar sensitivity. It should be possible to increase significantly the sensitivity of detection by the CCD: the excitation and emission filters could be matched more precisely to the absorbance and fluorescence wavelengths of ANTS. A higher power lamp could be used together with a lens with a wider aperture. The CCD could be cooled to a lower temperature. CCD cameras with secondary water cooling are available which operate at about 210° K. This alone should enable the lower detection limit to be about 4 fold less than at present.

The CCD system was more convenient to use than the photographic method since the gels could be imaged immediately after electrophoresis while they remained clamped in their glass electrophoresis cassettes. It was found convenient to image each gel firstly for 10 sec per section and subsequently for 60 sec. The CCD response is directly proportional to the exposure time and the shorter exposure times are required to avoid saturation of the CCD with light from the more intense bands. Fading of the fluorescence was found to be less than 1% when the gels were illuminated for up to 30 min. In contrast to the photographic method, a linear CCD response was obtained for fluorescent bands containing between 12.5 and 500 pmol. However there was considerable variation when attempting to measure 3.1 pmol of saccharide since the band fluorescence was close to the background level.

The method described should be particularly useful for the microscale analysis of numerous samples in parallel, for instance those obtained from the enzymological structural analysis of complex oligosaccharide. Although not all the isomers and epimers tested were separated, the demonstrated resolving power, the low cost and simplicity of the procedure, the widespread availability of the electrophoretic equipment, the sensitivity of the detection and the quantitative characteristics of the derivatisation make the method a useful addition to current cargohydrate analysis methods.

This method not only has considerable potential for further development itself but it also enables the use of the powerful technique of blotting. Initial experiments have shown that it is possible to transfer, both rapidly and efficiently, the ANTS derivatised saccharides from gels onto porous membranes for probing with specific carbohydrate binding proteins such as lectins and specific antibodies.

Example 2

Further work was carried out using the technique generally as described above, analysing the degradation products of the digestion of an oligosaccharide with two specific glycosidases. The further work uses an alternative electrophoretic system, based on that described by Neville (reference 8) in place of the Laemmli system.

Saccharides, at least 5 nmol of each per reaction tube, were derivatised in 5 ul of a solution of 0.2M ANTS (Molecular Probes Inc.) in glacial acetic acid/water (15:85, v/v) and 5 ul of 1.0M sodium cyanoborohydride solution in dimethylsuplhoxide. The solution was mixed well and incubated at 37° C. for 15 h. The reaction mixture was freeze-dried at approximately 45° C. in a centrifugal vacuum evaporator and dissolved in electrophoresis sample buffer consisting of 6M urea in 0.04M boric acid, 0.041 Tris(hydroxylmethyl)aminomethane (Tris) base buffer, pH 8.6 so that 1 ul contained 100 pmol of each derivatised saccharide.

Samples, 2 ul in volume, were electrophoresed using the discontinuous buffer system described by Neville (8). The resolving gel was 30% w/v acrylamide 0.8% w/v N,N'-methylenbisacrylamide and the stacking gel was one tenth of these concentrations. A Hoefer Scientific Instruments SE600 vertical slab gel apparatus was used. The resolving gel dimensions were 140 mm wide $\times$ 140 mm high by 0.5 mm and it was cooled by the surrounding analyte which had a temperature of approximately 7° C.

Samples were electrophoresed at 250 V for 30 min, then at 500 V for 30 mins and finally at 1500 V for approx 60 min. Electrophoresis was stopped when the band of unreacted ANTS reached approx 10 mm from the anodic edge of the gel.

This brightly fluorescent band could be seen from outside the elctrophoresis tank by illumination from a hand-held a u.v. lamp, max wavelength 360 nm, (U.V.P. Ltd). The fluorescent saccharide band patterns were viewed after removal from their glass cassettes by illuminating the gel on u.v. light box (Transilluminator, type TM40, max. wavelength 302 nm, UVP Ltd) and were photographed with a Polaroid type 55 film through a Wratten 8 filter (Kodak) with an aperture of f4.5 and an exposure time of 50 sec. Alternatively, gels were viewed while still in their pryrex glass electrophoresis cassettes using an Astromed 2200 cooled CCD imaging system. (Astomed Ltd, Cambridge U.K.).

The CCD was cooled to approximately 246° K. The gels were viewed for 10 sec and the images were processed digitally to minimise any unevenness across the gel in the intensity of the illumination. Full details of this methodology are given above.

The results of electrophoresis of various ANTS labelled sugars, including the standard mixture referred to above and also the products of digestion of oligosaccharide III (FIG. 14) with two glycosidases are shown in FIGS. 15 and 16. In FIG. 15 the lanes are as follows: lanes 1 and 10, the standard mixture. In increasing order of mobility the saccharides (all D configuration) are: (1) maltoheptaose, (2) maltohexaose, (3) maltopentaose, (4) maltotetraose, (5) maltotriose, (6) cellotriose, (7) galactobiose, (8) maltose, (9) lactose, (10) galactosylgalactose, (Gal alpha 1–4 Gal), (11) N-acetylgalactosamine (12) galactose, (13) glucose, (14) 6-deoxyglucose; lane 2, oligosaccharide III; lane 3, enzyme digestion buffer; lane 4, oligosaccharide III and neuraminidase; lane 5, neuraminidase; lane 6, oligosaccharide III and beta-galactosidase; lane 7, beta-neuraminidase; lane 5, neuraminidase; lane 6, oligosaccharide III and beta-galactosidase; lane 7, beta-galactosidase; lane 8, oligosaccharide III and neuraminidase and beta-galactosidase; lane 9, neuramindase and beta-galactosidase. Either 100 pmol of oligosaccharide III or an equivalent quantity of digestion product was loaded per gel lane. The broad band near the base of the gel is caused by excess unreacted ANTS.

FIG. 16 shows results obtained by viewing a gel with the Astromed cooled CCD imaging system.

For FIG. 16, the gel lanes were loaded in the same order and with the same samples as for the gel of FIG. 15. However, the orientation of the camera was such that the graphic display image was bilaterally inverted. Hence the gel lanes are numbered from right to left. The band of excess ANTS was outside the imaged area of the gel.

The high resolution of the electrophoresis is demostrated in lanes 1 and 10 of FIGS. 15 and 16, in which 14 saccharides ranging in size from 6-deoxyglucose to maltoheptaose are separated. Glucose and its straight chain alpha 1-4 linked oligomers from maltose to maltoheptaose were well separated. Various isomeric mono- di- and trisaccharides were also resolved. For instance, maltotriose (Glc alpha 1-4 Glc alpha 1-4 Glc) and cellotriose (Glc beta 1-4 Glc 1-4 Glc) were separated from each other, as were maltose (Glc alpha 1-4 Glc), lactose (Gal beta 1-4 Glc) and cellobiose (Glc beta 1-4 Glc). The epimers galactose and glucose were also well resolved. The mobilities of the ANTS labelled saccharides appears to depend primarily on their size but it is also influenced by their structures. It is possible that certain saccharide structures favour their interaction with the gel matrix, which could result in their electrophoretic retardation.

The electrophoretic buffer system described by Neville (8) in combination with 30% (w/v) uniform concentration acrylamide gave similar separation patterns and similar resolution to those obtained using the buffer system of Laemmli (1), as described above. The Neville system has the advantage in that the run time was approximately 30% less than that of the Laemmli system.

A demonstration of how this methodolgy can be used to analyse the degradation products arising from the action of specific glycosidases on a complex oligosaccharide is also given in FIGS. 15 and 16. Oligosaccharide III (see FIG. 14) (1 nmol) was dissolved in 10 ul 50 mM KCl, 1 mM dithiothreitol in 50 mM Na citrate buffer pH 6.0 and incubated at 37° C. for 20 h with either 10 mU of neuraminidase (EC 3.2.1.18) (Sigma, type X from *Clostridium perfringens*) (10 mU (suppliers definitions)/ul in H$_2$O or 1 U of beta-galactosidase (EC 3.2,1.23) Sigma, Grade VIII from *Escherichia coli*) (1 U (suppliers definition) /ul in 1.0 m Na phospate buffer, pH 7.3) or a mixture of similar quantities of the two enzyme.

Digestion of oligosaccharide III by neuraminidase alone produced a new band having a lower mobility than the original oligosaccharide (FIGS. 15 and 16, lane 4). Presumably this reflects the loss from the oligosaccharide of the negative Charge on the released N-acetylneuraminic acid which more than compensates for the reduction in its size. The digestion was incomplete under the conditions used; some oligosaccharide III remained (FIGS. 15 and 16, lane 4). The N-acetylneuraminic acid should not be detected by the ANTS labelling procedure, although a faint new band having a mobility slightly less than galactose and of unknown identity was produced. Beta-galactosidase alone had no effect on the oligosaccheride (FIGS. 15 and 16, lane 6). However, a combination of neuraminidase and beta-galactosidase gave incomplete digestion and produced three degradation products (FIGS. 15 and 16, lane 8).

The bend with the lowest mobility represents the original oligosaccharide minus the N-acetylneuraminic acid as when digested with neuraminidase alone.

The bend with the next highest mobility represents the oligosaccharide after loss of both neuraminic acid and then galactose. This latter band had a mobility slightly greater than the original oligossacheride band and their difference can be seen by close inspection of lanes 4, 6 and 8 in FIGS. 15 and 16. When both glycosidases were used together none of the original oligosaccharide was detectable. The degradation product with the highest mobility was the released galactose which can be seen to align with the band of galactose in the standard mixture. Faint artefactual bands were visible in some gel lanes. One faint band which had a mobility close to oligosaccharide III can be seen in gel lanes 2 to 9 in FIGS. 15 and 16 and was an aid in assessing the relative mobilities of oligosaccharide III and its degradation products.

These experiments demonstrate both the high resolution of the electrophoretic method and how it can be used in the structural analysis of oligosaccharides. Although not all of the saccharides which have been tested are separated, (e.g. galactose and mannose), the specifities of the enzymes used should enable unequivocal identification of degradation products. The method allows the high resolution analysis of multiple samples in parallel and is relatively rapid, sensitive and inexpensive and may make glycan structural analysis available more widely. It has also been show that the ANTS derivatisation of small saccharides is virtually quantitative and that approximately 1 pmol can be detected photographically and as little as 0.2 pmol using the cooled CCD imaging system. The method should, therefore be useful for the analysis of oligosaccharide from many biological sources.

Example 3

Charged saccharides in the form of heparin fragments from partial nitrous acid digests are reacted with ANSA to form conjugates. The reaction is carried out in 10 to 100 mM sodium acetate buffer (pH 5.0). The heparin fragments are present in an amount of 0.01–1 umol/ml and are reacted with ANSA and sodium cyanoborohydride in a ten fold molar excess with respect to the reducing end sugar of the heparin fragment. The derivatized heparin fragments are then subjected to electrophoretic resolution in 40% acrylamide/5% bis gels, with a Tris/glycine buffer system (25 mM Tris, 195 mM glycine, pH 8.3). The electrophoretic gel is run at 300 volts for approximately 90 minutes.

Example 4

Neutral saccharides in the form of tetrose derived from asialo-GM1 where charged by reacting them with ANSA to form conjugates. The reaction conditions were 10 to 100 mM sodium acetate buffer (pH 5.0), asialo-GM1 at 0.01-1 uM/ml, ANSA and sodium cyanoborohydride in tenfold molar excess to the reducing end of the sugar. Derivatised saccharides were resolved in 40% acrylamide/5% bis gels with a Tris/glycine buffer system (25 mM Tris, 195 mM glycine, pH 8.3) run at 300 volts for approximately 90 minutes.

All of the sugars referred to in the specification are D isomers unless otherwise specified.

TABLE 1

| Saccharides analysed Abbreviated formula | Trivial name |
| --- | --- |
| 1 2-deoxy-D-Gal | 2-deoxygalactose |
| 2 6-deoxy-L-Gal | L-fucose |
| 3 2-deoxy-D-Glc | 2-dexoyglucose |
| 4 6-deoxy-D-Glc | 6-deoxyglucose |
| 5 D-Gal | galactose |
| 6 α-D-Glc | glucose |
| 7 D-Man | mannose |
| 8 3-O-methyl- -D-Glc | 3-O-methylglucose |
| 9 D-GalNac | N-acetylgalactosamine |
| 10 α-D-GlcNac | N-acetylglucoseamine |
| 11 D-GlcNac6SO$_3$ | N-acetylglucosamine-6-sulphate |
| 12 α-D-Gal-(1-4)-D-Gal | galactosylgalactose |
| 13 B-D-Gal-(1-6)-D-Gal | galactobiose |
| 14 B-D-Gal-(1-4)-D-Glc | lactose |

TABLE 1-continued

| Saccharides analysed Abbreviated formula | Trivial name |
|---|---|
| 15 α-D-Gal-(1-6)-D-Glc | mellibiose |
| 16 B-D-Gal-(1-4)-D-Man | galactosylmannose |
| 17 α-D-Glc-(1-3)-D-Glc | nigerose |
| 18 B-D-Glc-(1-3)-D-Glc | laminaribiose |
| 19 α-D-Glc-(1-4)-D-Glc | maltose |
| 20 B-D-Glc-(1-4)-D-Glc | cellobiose |
| 21 α-D-Glc-(1-6)-D-Glc | isomaltose |
| 22 B-D-Glc-(1-6)-D-Glc | gentiobiose |
| 23 α-D-Man-(1-3)-D-Man | mannobiose |
| 24 B-D-Gal-(1-4)-D-GlcNac | N-acetyllactosamine |
| 25 B-D-GlcNac-(1-4)-D-GlcNac | diacetylchitobiose |
| 26 α-D-Glc-(1-4)-α-D-Glc-(1-4)-α-D-Glc | maltotriose |
| 27 B-D-Glc-(1-4)-B-D-Glc-(1-4)-α-D-Glc | cellotriose |
| 28 α-D-Glc-(1-6)-α-D-Glc-(1-4)-α-D-Glc | panose |
| 29 α-D-Glc-(1-6)-α-D-Glc-(1-6)-α-D-Glc | isomaltotriose |
| 30 B-D-Gal3Neu5AC-(1-4)-D-Glc | N-acetylneuraminlac |
| 31 (α-D-Glc-(1-4)-)$_3$-D-Glc | maltotetraose |
| 32 α-D-Glc-(1-6)-(α-D-Glc-(1-4)-)$_2$α-D-Glc | |
| 33 (α-D-Glc(-(1-4)-)$_4$-D-Glc | maltopentaose |
| 34 (α-D-Glc(-(1-4)-)$_5$-D-Glc | maltohexaose |
| 35 (α-D-Glc(-(1-4)-)$_6$-D-Glc | maltoheptaose |

References

1. Laemmli, U.K. (1970) Nature 227, 680–685
2. Jackson, P., Urwin, V. E. & Mackay, C. D. (1988) Electrophoresis 9, 330–339.
3. Rice, K. G. Rotrink, M. K. and Linhardt, R. J. (1987) Biochem. J. 244, 515–522
4. Turnbull, J. E. and Gallagher, J. T. (1988) Blochem. J. 251, 597–608
5. Al-Hakim, A. and Linhardt, R. J. (1988) Electrophoresis II 23–28
6. Weitzman, S., Scott, V. & Keegstra, K. (1979) Anal. Biochem. 97, 438–449
7. Hardy M. R. & Townsend, R. R. (1988) Proc. Nat. Acad. Sci. 85, 3278–3293
8. Neville, Jr., D. M., J. Biol. Chem. 1971, 246, 6328–6334.

I claim:

1. A method of separating or distinguishing analyzing carbohydrate substance mixtures, comprising labelling carbohydrate substances with a labelling reagent comprising a fluorescent naphthalene ring structure having as a substituent a reactive group capable of reacting with a reducing sugar to bind thereto and also having at least one substituent group capable of carrying a charge but which does not react with reducing sugars and does not extinguish fluorescence of the labelling reagent; applying the labelled substances to an electrophoretic gel; and running the gel to cause differential migration of different substances.

2. A method according to claim 1, wherein the reactive group is an amino group.

3. A method according to claim 2, wherein the amino group is attached to an alpha carbon of the naphthalene.

4. A method according to claim 1, wherein the group capable of carrying a charge is a sulphonic acid group.

5. A method according to claim 4, wherein the labelling reagent is 8-aminonaphthalene-1,3,6-trisulphonic acid.

6. A method according to claim 4, wherein the labelling reagent is 1-amino-4-naphthalene sulphonic acid.

7. A method according to claim 4, wherein the labelling reagent is a 1-amino-naphthalene disulphonic acid.

8. A method according to claim 1, wherein the labelling reagent further comprises one or more non-reactive substituent groups attached to the napthalene ring structure.

9. A method according to claim 1, wherein the electrophoretic gel comprises a polyacrylamide gel having a concentration in the range of 15% to 60%.

10. A method according to claim 9, wherein the gel has a concentration in the range 20% to 40%.

11. A method according to claim 9 or 10, wherein the gel is cross linked with N,N' methylebenbisacrylamide.

12. A method according to any one of the preceding claims, wherein electrophoresis is carried out using a stacking buffer system.

13. A method according to claim 1, wherein the labelled carbohydrate substances are imaged with a charge coupled device.

14. A method according to claim 1, wherein the carbohydrate substances are derived from glycoproteins, proteoglycans, glycolipids, glycosphingolipids, polysaccharides, and glycosaminoglycans.

* * * * *